United States Patent [19]

Karoum et al.

[11] Patent Number: 4,863,962
[45] Date of Patent: Sep. 5, 1989

[54] D-DOPA, PHARMACEUTICALLY ACCEPTABLE SALTS THEREOF, AND METHODS OF TREATING PARKINSON'S DISEASE

[75] Inventors: Farouk Karoum, Alexandria, Va.; Erminio Costa, Chevy Chase, Md.

[73] Assignee: Fidia-Georgetown Institute for the Neurosciences, Washington, D.C.

[21] Appl. No.: 163,246

[22] Filed: Mar. 2, 1988

[51] Int. Cl.[4] .......................................... A61K 31/195
[52] U.S. Cl. ..................................................... 514/561
[58] Field of Search ......................................... 514/561

[56] References Cited

U.S. PATENT DOCUMENTS

| Re. 29,892 | 1/1979 | Bayne | 514/561 |
|---|---|---|---|
| 3,253,023 | 5/1966 | Wysong | 514/561 |
| 3,405,159 | 10/1963 | Krieger et al. | 514/561 |
| 3,557,292 | 1/1971 | Bartholini | 514/561 |
| 3,911,137 | 10/1975 | Miki et al. | 514/561 |
| 4,409,233 | 10/1983 | Tsukada et al. | 514/561 |
| 4,424,235 | 1/1984 | Sheth et al. | 514/561 |
| 4,497,826 | 2/1985 | Narabayashi et al. | 514/561 |

OTHER PUBLICATIONS

Chem. Abst. 88-124414j, (1988).
*Physician's Desk Reference*, 41st edition, 1987, pp. 1336-1337.
"Fitness," *Parade Magazine*, Mar. 1, 1987.
Yamada et al: "Studies on Optically Active Amino Acids".
Lloyd et al: *Journal of Pharm. and Exp. Ther.*, vol. 195: No. 3.
Lovenberg et al, *J. Biol. Chem.*, vol. 237, No. 1, 1962.

*Primary Examiner*—Stanley J. Friedman
*Attorney, Agent, or Firm*—Birch, Stewart, Kolasch & Birch

[57] ABSTRACT

The present invention is directed to a method of treating Parkinson's disease. More particularly, the present invention utilizes D-DOPA or the racemic mixture of D,L-DOPA, or pharmaceutically acceptable salts thereof, in an anti-parkinsonism effective amount for the treatment of Parkinson's disease.

6 Claims, No Drawings

D-DOPA, PHARMACEUTICALLY ACCEPTABLE SALTS THEREOF, AND METHODS OF TREATING PARKINSON'S DISEASE

SUMMARY OF THE INVENTION

The present invention is directed to a method of treating Parkinson's disease. More particularly, the present invention utilizes D-DOPA or the racemic mixture of D,L-DOPA and pharmaceutically acceptable salts thereof in an anti-parkinsonism effective amount for the treatment of Parkinson's disease.

BACKGROUND OF THE INVENTION

Heretofore, it has been known to treat Parkinson's disease with combination therapy utilizing L-DOPA and carbidopa. Parkinson's disease is believed to be a result of cholinergic overactivity due to a major derangement of the metabolism of dopamine and its synthesizing enzymes in the corpus striatum. Administration of dopamine, alone, is not an effective therapy since dopamine does not cross the blood brain barrier. L-DOPA, on the other hand, does cross the blood brain barrier where it is presumably converted to dopamine in the basal ganglia. However, only a small percentage of orally administered L-DOPA actually crosses the blood brain barrier due to the peripheral conversion of L-DOPA to dopamine by L-amino acid decarboxylase. Further, administration of L-DOPA is almost always associated with untoward side effects such as nausea, vomiting, hypotension, abnormal movements, and behavioral changes. In order for sufficient amounts of L-DOPA to cross the blood brain barrier, large doses of L-DOPA are required. Large doses of L-DOPA exacerbate these untoward side effects. In an attempt to overcome these problems, carbidopa is administered simultaneously with L-DOPA to inhibit peripheral decarboxylation of L-DOPA to dopamine, thus allowing greater quantities of a lower dose of L-DOPA to cross the blood brain barrier. Unfortunately, co-administration of L-DOPA plus carbidopa results in the same side effects as when L-DOPA is administered alone, only to a lesser extent.

BRIEF DESCRIPTION OF THE INVENTION

It is an object of the present invention to provide a therapy for Parkinson's disease which further decreases the dosage and the untoward side effects associated with the prior art therapies. The therapeutic benefits of L-DOPA in the treatment of Parkinson's disease are believed to result from the ability of L-DOPA to increase striatal dopamine content via decarboxylation of L-DOPA by L-amino acid decarboxylase. Use of L-DOPA in the therapy of Parkinson's disease is the result of extensive studies which show that the enzyme L-amino acid decarboxyase is stereospecific for the L-isomer. In view of this finding D-DOPA would not be expected to generate dopamine as effectively as L-DOPA.

However, as a result of the research of the present inventors, it was unexpectedly and surprisingly found that the administration of equal amounts of deuterated D,L-DOPA and L-DOPA increased rat brain deuterated dopamine content to about the same extent. It was also surprisingly found that the administration of D-DOPA increases striatal dopamine content to the same extent as L-DOPA.

DETAILED DESCRIPTION OF THE INVENTION

The present invention utilizes D-DOPA or the racemic mixture of D,L-DOPA, alone, or in combination therapy with a peripheral aamino acid decarboxylase inhibitor. Carbidopa is suitable peripheral amino acid dcarboxylase inhibitor carbidopa for the treatment of Parkinson's disease. D-DOPA is readily available from Aldrich (Milwaukee, Wis.). D-DOPA can also be isolated from a racemic mixture of D,L-DOPA according to the procedures set forth in U.S. Pat. No. 3,405,159. A further method for the chemical preparation of D-DOPA is set forth in Yamada et al., Chem. Pharm. Bull., Vol. 10, No. 8, 693 (1962). The pharmaceutically acceptable salts can be prepared by reacting D-DOPA with an acid such as hydrochloric acid.

In Vivo Studies

In order to show the effectiveness of D-DOPA for increasing striatal dopamine content, male Sprague-Dawley Rats (Zivic-Miller, Allison Park, Pennsylvania) weighing 300 to 400 grams were used. At least four weeks prior to the experiments, unilateral substantia nigra lesions were produced with intranigral administration of 6-hydroxydopamine according to the procedures set forth in Ungerstedt, Acta Physiol. Scand. (Suppl.) 367, 69 (1971).

The extent of unilateral substantia nigra lesions was tested by measuring apomorphine simulated rotation according to the procedures described in Understedt, supra, 1971; Freed et al. Ann. Neurol. 8, 516 (1980).

Either D- or L-DOPA was intragastrically administered to the rats in combination with carbidopa at doses of 50 mg/kg body weight of D-DOPA or L-DOPA and 5 mg/kg body weight of carbidopa, suspended in sterile water, to provide a pharmaceutically acceptable solution for administration. D- or L-DOPA was intragastrically administered to groups of five rats, which were sacrificed one or two hours after treatment. The left (intact) and right (lesioned) striata of these rats were excised and analyzed separately for the content of dopamine and its metabolites, 3,4-dihydroxyphenylacetic acid (DOPAC) and homovanillic acid (HVA), according to the procedure as set forth in Karoum, Neuromethods, Vol. 2 (G. B. Baker, A. A. Boulton and J. M. Baker eds.), The Humana Press, Inc., New Jersey, page 305, 1985.

TABLE 1

THE EFFECTS OF (L-DOPA + CARBIDOPA) AND (D-DOPA + CARBIDOPA) ON STRIATAL CONCENTRATION OF DOPAMINE, DOPAC AND HVA IN RATS WITH UNILATERAL SUBSTANTIA NIGRA LESIONS

| Description | Dopamine | | DOPAC | | HVA | |
|---|---|---|---|---|---|---|
| | Intact Striatum | Lesioned Striatum | Intact Striatum | Lesioned Striatum | Intact Striatum | Lesioned Striatum |
| Unilaterally Lesioned Rats (ULR) | 150 ± 8.3 | 4.5 ± 1.4 | 17 ± 0.9 | 0.8 ± 0.3 | 6.9 ± 1.5 | 1.0 ± 0.3 |

TABLE 1-continued

THE EFFECTS OF (L-DOPA + CARBIDOPA) AND (D-DOPA + CARBIDOPA) ON STRIATAL CONCENTRATION OF DOPAMINE, DOPAC AND HVA IN RATS WITH UNILATERAL SUBSTANTIA NIGRA LESIONS

| Description | Dopamine | | DOPAC | | HVA | |
|---|---|---|---|---|---|---|
| | Intact Striatum | Lesioned Striatum | Intact Striatum | Lesioned Striatum | Intact Striatum | Lesioned Striatum |
| ULR 1 Hour After L-DOPA plus Carbidopa[a] | 180 ± 5.1* | 2.0 ± 0.2 | 38 ± 4.8* | 12 ± 2.6** | 26 ± 3.3** | 11 ± 1.8** |
| ULR 1 Hour After D-DOPA plus Carbidopa[b] | 170 ± 11.2 | 3.4 ± 0.7 | 46 ± 4.8** | 17 ± 2.2** | 27 ± 2.3** | 11 ± 1.8** |
| ULR 2 Hour After L-DOPA plus Carbidopa[a] | 160 ± 5.8 | 2.5 ± 1.0 | 22 ± 2.2* | 5.6 ± 1.4** | 13 ± 1.2** | 4.7 ± 0.9** |
| ULR 2 Hour After D-DOPA plus Carbidopa[b] | 190 ± 4.2* | 2.8 ± 1.1 | 18 ± 1.6 | 4.5 ± 1.1** | 10 ± 0.9 | 4.3 ± 0.7** |

All results are in (mean ± SEM) ng/mg protein.
*$p < 0.05$, compared with untreated unilaterally lesioned rats.
**$p < 0.005$, compared with untreated unilaterally lesioned rats. by unpaired t-test
[a]L-DOPA consisted of 50 mg/kg of L-DOPA plus 5 mg/kg of carbidopa.
[b]D-DOPA consisted of 50 mg/kg of D-DOPA plus 5 mg/kg of carbidopa.
L- and D-DOPA were administered intragastrically in a water suspension. Rats in groups of five were sacrificed 1 or 2 hours after treatment.

As can be seen by the results summarized in Table 1, intragastric administration of D- and L-DOPA increased the concentrations of dopamine and its metabolites in the intact striata of the unilaterally lesioned rats to about the same extent, but there appeared to be a delay in the time required for D-DOPA to produce its maximal effect. Thus, as shown in Table 1, dopamine content in the intact striata peaked atone hour after L-DOPA administration, and peaked at two hours after administration in the case of D-DOPA. Neither D- nor L-DOPA increased dopamine concentrations in the lesioned striata. Rather, dopamine concentrations were greatly reduced as a result of the unilateral lesion of the substantia nigra. The concentrations of DOPAC and HVA in the lesioned striata were markedly increased by both D- and L-DOPA one hour after treatment and then rapidly declined two hours later, indicating that the formation of dopamine from D- and L-DOPA in the striatum reached its maximum concentration within one hour after intragastric administration.

Since L-amino acid decarboxyase is stereospecific, direct decarboxylation by the enzyme cannot conceivably account for substantial formation of dopamine from D-DOPA. In an attempt to find the alternate pathways, four groups of Sprague-Dawley rats weighing 120–50 grams with cannulae permanently implanted into their lateral ventricles, according to the procedure described in Robinson et al., *Physiol. Behav.* 4, 123–124, (1969), were used. One group received 10μ of saline into the ventricles. The second, third and fourth groups received, intraventricularly, 200 μg of L-DOPA, D-DOPA and 3,4-dihydroxyphenylpyruvic acid (DHPPA) in 10 μl saline, respectively. The rats were sacrificed two hours after treatment and their striata removed and analyzed. Striatal concentrations of dopamine, DOPA and HVA were measured by mass fragmentography according to the procedure set forth in Karoum, *Neuromethods*, supra.

TABLE 2

THE EFFECTS OF INTRAVENTRICUALP ADMINISTRATION OF D-DOPA, L-DOPA AND 3,4-DIHYDROXYPHENYLPYRUVIC ACID (DHPPA) ON STRIATAL DOPAMINE AND ITS METABOLITES

| Description | Dopamine | DOPAC | HVA |
|---|---|---|---|
| Control Rats | 99 ± 1.4 | 16 ± 0.43 | 5.2 ± 0.23 |
| Intraventricular L-DOPA[a] | 120 ± 7.4* | 59 ± 9.49* | 22.2 ± 1.60* |
| Intraventricular D-DOPA[a] | 116 ± 5.1* | 19 ± 0.92 | 4.8 ± 0.50 |
| Intraventricular DHPPA[a] | 140 ± 11.0* | 96 ± 16.6* | 23.3 ± 3.53* |

All results are in (mean ± SEM) ng/mg protein.
[a]200 μg of each of L-DOPA, D-DOPA or DHPPA in volumes of 10 μl was injected intraventricularly via permanently implanted cannulae in the ventricles. The rats were sacrificed two hours after treatment and their brains removed.
*$p < 0.05$ compared to the controls by analysis of variance employing the Bonferroni correction.

As seen from Table 2, all three treatments significantly increased the striatal concentrations of dopamine and its metabolites. The increases in DOPAC and HVA produced were higher for L-DOPA and 3,4-dihydroxyphenylpyruvic acid (DHPPA) than for D-DOPA. The results indicate that DHPPA is readily converted to dopamine in the brain. In fact, intraventricular administration of DHPPA produced larger elevations of dopamine and DOPAC than did either D- or L-DOPA. On the other hand, repeated intragastric administration of DHPPA plus carbidopa (50 mg/kg of each for four days) did not increase striatal dopamine or its metabolites, confirming that DHPPA does not easily cross the blood brain barrier. Hence, if DHPPA is an intermediate in the conversion of D-DOPA to dopamine, the metabolic changes involved probably occur within the brain.

The accumulation of dopamine in the striatum of rats receiving DHPPA intraventricularly, taken together with the wide distribution of the transamination reaction in both the brain and peripheral tissues, favorably supports the possible involvement of DHPPA in the formation of dopamine from D-DOPA. DHPPA can be formed from D-DOPA by either of two pathways, that is, direct transamination, or through deamination by D-amino acid oxidase, an enzyme widely distributed in the brain. In this context it should be mentioned that the pattern of changes of striatal dopamine and its metabolites observed after intragastric administration of D- and L-DOPA are similar to those observed in the hypothalamus. Both amino acids increase hypothalamic dopamine by similar amounts, while the increases in DOPAC and HVA are considerably higher after administration of L-DOPA than after the administration of D-DOPA.

The present inventors have studied the effects of carbidopa on the urinary excretion of dopamine after the administration of D- and L-DOPA alone, (50 mg/kg). Carbidopa reduced the excretion of dopamine following D-DOPA to a far greater degree than when carbidopa was co-administered with L-DOPA as set forth in Karoum et al., *Brain Research*, 1987, in press. These results suggest that the pathways responsible for the formation of dopamine from D-DOPA in the periphery are more sensitive to carbidopa than are the pathways that convert L-DOPA to dopamine. Hence, one might expect that in rats receiving equal doses of either stereoisomer, proportionately more D-DOPA than L-DOPA will cross into the brain when each of these amino acids is co-administered with carbidopa.

The unexpected ability of D-DOPA to elevate striatal concentrations of dopamine suggests that D-DOPA offers advantages over L-DOPA in the treatment of Parkinson's disease. For example, the peripheral undesirable side effects normally associated with L-DOPA treatment e.g., nausea, vomiting, cardiac arrthymias, hypotension and diarrhea could be lessened by the use of D-DOPA. Furthermore, since in the brain the conversion rate of D-DOPA to dopamine is slower than that of L-DOPA, a more adequate dosing system can be achieved and, hence, a better steady state concentration of striatal dopamine can be obtained.

The compounds (i.e., D-DOPA or the racemic mixture of D,L-DOPA) utilized in the present invention may be formulated into pharmaceutical compositions by combination with appropriate pharmaceutically acceptable carriers or diluents, and may be formulated into preparations in solid, semisolid, or liquid forms such as tablets, capsules, powders, granules, solutions, suppositories, or injections, in the usual ways for oral or parenteral administration. The following methods and excipients are merely exemplary and are in no way limiting.

In pharmaceutical dosage forms, the compounds employed in the present invention may be used in the form of their pharmaceutically acceptable salts, and also may be used alone or in appropriate association, as well as in combination with other pharmaceutically active compounds such as carbidopa and other peripheral amino acid decarboxylase inhibitors.

In the case of oral preparations, the compounds may be used alone or combined with appropriate additives to make tablets, powders, granules or capsules, e.g., with conventional additives such as lactose, mannitol, corn starch or potato starch; with binders, such as crystalline cellulose, cellulose derivatives, acacia, corn starch or gelatins; with distintegrators such as corn starch, potato starch or sodium carboxymethylcellulose; with lubricants such as talc or magnesium stearate; and if desired, with diluents, buffering agents, moistening agents, preservatives and flavoring agents.

Furthermore, they may be made into suppositories by mixing with a variety of bases such as emulsifying bases or water-soluble bases.

The compounds used in the present invention may be formulated into preparations for injections by dissolving, suspending or emulsifying them in aqueous or non-aqueous solvents, such as vegetable oil, synthetic aliphatic acid glycerides, esters of higher aliphatic acids or propylene glycol; and if desired, with conventional additives such a solubilizers, isotonic agents, suspending agents, emulsifying agents, stabilizers and preservatives.

The suitable dose of D-DOPA varies with the subject, drug form, method and period of administration. However, in order to obtain desirable effects, generally it is recommended to administer the D-DOPA in amounts of 10–50 mg/kg body weight. More particularly, it is recommended to administer 100–500 mg D-DOPA per day.

The following examples illustrate pharmaceutical preparations which can be made and utilized in the present invention.

EXAMPLE 1

2000 g of D-DOPA, 1500 g of microcrystalline cellulose (Avicel-PH-101), 100 g of stearic acid and 200 g of colloidal silica are granulated and blended. Tablets are punched using a 7/16 inch standard concave punch to obtain 10,000 tablets each containing 20% mg of D-DOPA.

EXAMPLE 2

2.0 g of D-DOPA hydrochloride is dissolved in 300 ml of sterile water. 30 ml or 1 fluid ounce doses equaling ten 200 mg doses of D-DOPA, was thus obtained.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method of treating Parkinson's disease which comprises administering to a patient suffering from this disease an anti-parkinsonism effective amount of D-DOPA.

2. A method of treating Parkinson's disease which comprises administering to a patient suffering from this disease an anti-parkinsonism effective amount of a composition comprising D-DOPA and a pharmaceutically acceptable carrier or diluent.

3. The method according to claim 1 which comprises co-administering D-DOPA with an effective amount of a peripheral amino acid decarboxylase inhibitor.

4. The method according to claim 1, wherein the D-DOPA or D,L-DOPA is administered in an amount of 50 mg/kg body weight.

5. The method according to claim 1, wherein the D-DOPA and/or D,L-DOPA is administered in an amount of 100 to 500 mg per day.

6. The method according to claim 3, wherein said peripheral amino acid decarboxylase inhibitor is carbidopa.

* * * * *

UNITED STATES PATENT AND TRADEMARK OFFICE
CERTIFICATE OF CORRECTION

PATENT NO. : 4,863,962

DATED : September 5, 1989

INVENTOR(S) : Farouk KAROUM and Erminio COSTA

It is certified that error appears in the above-identified patent and that said Letters Patent is hereby corrected as shown below:

Column 6, line 56:

Claim 4

Line 2, delete "or D,L-DOPA".

Column 6, line 59:

Claim 5

Line 2, delete "and/or D,L-DOPA".

Signed and Sealed this

Ninth Day of July, 1991

Attest:

HARRY F. MANBECK, JR.

Attesting Officer

Commissioner of Patents and Trademarks